United States Patent [19]
Ali

[11] Patent Number: 5,505,091
[45] Date of Patent: Apr. 9, 1996

[54] HURRICANE SIMULATION TESTING APPARATUS

[76] Inventor: Wakar Ali, 8532 NW. 64th St., Miami, Fla. 33166

[21] Appl. No.: 416,631

[22] Filed: Apr. 5, 1995

[51] Int. Cl.$^6$ .............................. G01L 7/00; G01N 3/02
[52] U.S. Cl. .................................................. 73/714; 73/856
[58] Field of Search ........................... 73/147, 714, 856, 73/857, 859, 860; 417/110, 117, 179, 180

[56] References Cited

U.S. PATENT DOCUMENTS

| | | | |
|---|---|---|---|
| 1,834,073 | 12/1931 | Senna | 73/856 |
| 2,565,371 | 8/1951 | Hollis | 73/857 |
| 4,358,249 | 11/1982 | Hanson | 417/179 |

Primary Examiner—Richard Chilcot
Assistant Examiner—William L. Oen
Attorney, Agent, or Firm—Robert M. Downey

[57] ABSTRACT

An apparatus for testing the strength and performance of various building structures, such as doors, windows, storm shutters and panels, under hurricane type conditions, the apparatus including a vertically supported wall and a movable test structure mounting and support assembly including a frame for supporting a building structure to be tested. The frame is movably attachable in sealed engagement to a front face of the wall, such that the test structure is disposed in close, spaced relation to the wall, creating an air tight cavity between the building structure and the front face, wherein airflow is selectively delivered to or removed from the cavity by a diverter valve along an airflow conduit connecting between an air passage hole in the wall and to a high volume, low pressure blower. A computer controls the diverter valve and monitors pressure in the cavity to selectively control and rapidly change the cavity pressure through a range of predetermined positive and negative pressure levels.

11 Claims, 2 Drawing Sheets

HURRICANE SIMULATION TESTING APPARATUS

BACKGROUND OF THE INVENTION

1. Field of the Invention

The present invention relates to a hurricane simulation testing apparatus and more specifically to an apparatus for testing building structures such as doors, windows, storm panels, hurricane shutters and the like, under hurricane type conditions to measure the strength and integrity of the structures under such conditions.

2. Description of the Related Art

In many coastal areas and regions where the risk of hurricanes is prevalent, building codes require that various structures on houses and buildings be able to withstand hurricane type conditions within predetermined parameters. In particular, Dade County, Florida has recently revised it's building code in response to the devastation experienced as a result of hurricane Andrew. The Dade County building code, which is the most rigorous in the country and is recognized by most other counties and municipalities, sets forth specific standards for building structures such as aluminum garage doors, windows, storm panels and hurricane shutters. In accordance with the building code, these various structures must withstand certain hurricane type conditions under a series of tests including subjecting the structure to increments of pressure, cycling of pressure and an impact test.

Prior to the new building code, various specified structures were only required to be subject to certain pressure tests. Typically, this has been done using a pressure chamber which is essentially a room having four side walls, a floor, a ceiling and an interior chamber of significant volume. The structure to be tested is mounted, facing inwardly, in a window opening on one of the side walls. For instance, when testing a garage door using this type of system, it is necessary to mount the outside of the garage door facing in towards the interior chamber so that the outside of the door will be subjected to the pressure conditions. With the test structure mounted, a large volume of airflow is either introduced to the interior chamber to increase pressure or, alternatively, the air is evacuated to create a negative pressure.

Pursuant to the building code test requirements, the increments of pressure test requires subjecting the structure to various increments of pressure between 0 to 500 PSF, maintaining the pressure for 30 seconds at the maximum pressure. The cycling of pressure test requires subjecting the structure to rapid changes of pressure between 0 and a defined maximum pressure throughout a series of repetitions. For instance, it may be required to subject the structure to a rapid increase of pressure from 0–25 PSF, for 700 cycles, with each cycle being completed within 3 seconds. Next, the structure would be subject to 10 cycles between 0–35 PSF and thereafter 1 cycle between 0–65 PSF. The specific number of cycles and maximum pressure levels depend on the product being tested and the elevation above ground level at which the product is expected to be used.

The new building code now requires, in addition to the increments of pressure test and cycling of pressure test, an impact test, wherein the structure must be subject to impact by an 8 foot long 2"×4", fired at the structure at a predetermined velocity. Under each of the tests, inductive displacement transducers are used to measure the deflection of the structure at various designated locations. The requirements of the new building code present several problems when using a conventional air pressure testing chamber to test a particular specimen structure. In particular, the new code requires that each cycle, in the cycling of pressure test, be completed within 3 seconds. The conventional air pressure chambers, having a significantly large volume, require very high volume pumps to complete cycling within the required 3 second limit. Further, pressure testing requires the test specimen to be mounted with the outside of the specimen facing inwardly towards the pressure chamber. Accordingly, the impact test, required by the new building code, cannot be performed on the test specimen while mounted to the chamber, as the outside of the specimen (e.g. garage door) is not accessible. Thus, to perform the impact test, it is required to remove the test specimen from the air pressure chamber and remount the test specimen on another support structure. When performing the various tests on a large number of products, this procedure can prove to be expensive, time consuming and impractical.

Accordingly, there is a need for a test apparatus specifically structured to subject various test specimens to hurricane type conditions as required by new building codes, wherein cycling of pressure and impact tests can be performed rapidly and efficiently.

SUMMARY OF THE INVENTION

The present invention is directed to a hurricane simulation testing apparatus which is specifically structured and designed for testing the strength and integrity of various building structures, such as windows, garage doors, hurricane shutters, storm panels, entry doors and the like under hurricane type conditions. The test apparatus of the present invention includes a vertically supported wall and a movable test specimen mounting and support assembly including a frame structured to support a building structure specimen to be tested. The frame includes an outer face and an opposite inner face and an interior mounting zone defined within and surrounded by the frame. The inner face of the frame is removably attachable in sealed engagement to a front face of the wall, with the test specimen disposed in close, spaced relation to the front face, creating an air-tight cavity of relatively small volume between the building structure and front face. The wall includes at least one air passage hole formed therethrough and in fluid flow communication with the cavity formed when the frame and test specimen are attached to the wall. A high volume, low pressure blower for generating a high volume airflow is interconnected with the cavity by an airflow conduit or hose extending between the blower and the air passage hole at the rear face of the wall. A diverter valve is disposed inline along the airflow conduit and is specifically structured to control airflow including direction of airflow, to and from the cavity. A pressure sensor interconnected with the cavity measures pressure levels within the cavity and delivers the pressure data to a computer. The computer monitors the pressure in the cavity and controls operation of the diverter valve so as to selectively control airflow to or from the cavity. In this manner, the cavity pressure is rapidly controlled through a range of predetermined positive and negative pressure levels.

With the foregoing in mind, it is a primary object of the present invention to provide a hurricane simulation testing apparatus which is highly versatile and efficient, and including a relatively small volume air cavity or chamber to facilitate rapid cycling of pressure.

It is a further object of the present invention to provide a highly versatile hurricane simulation testing apparatus enabling a test specimen to be subjected to an increment of pressure test, a cycling of pressure test and an impact test without removal or remounting of the test specimen between any of the required tests.

It is a further object of the present invention to provide a hurricane simulation testing apparatus for testing the strength and integrity of various building structures including windows, garage doors, hurricane shutters, storm panels, entry doors and the like, wherein the apparatus is specifically structured and designed to occupy a minimal amount of space while enabling all required tests, under building code requirements, to be performed rapidly, efficiently and systematically.

These and other objects and advantages of the present invention will be more readily apparent in the detailed description which follows.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

Figure 1:
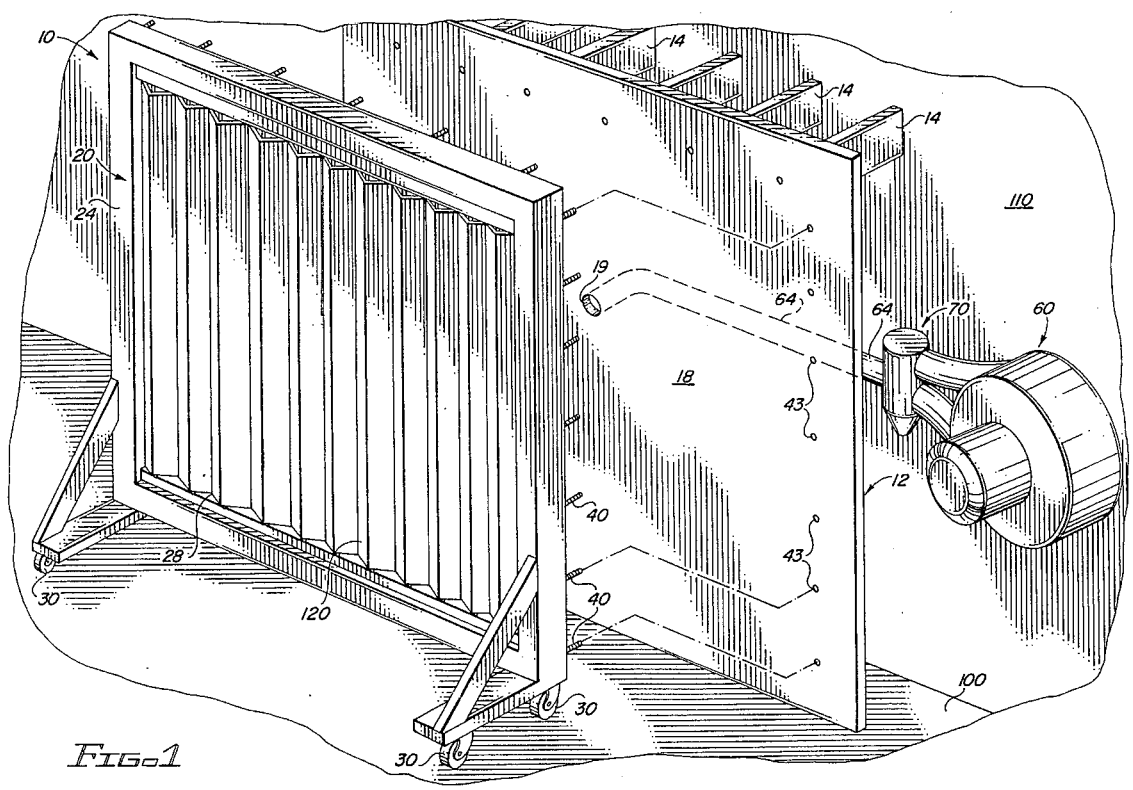
FIG. 1 is a front, exploded view shown in perspective of the apparatus of the present invention.
Figure 2:
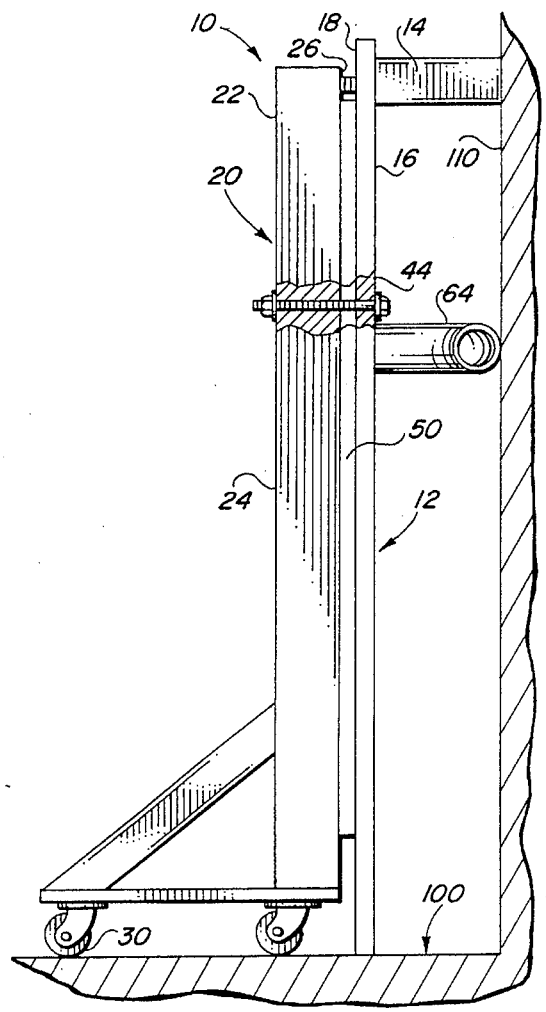
FIG. 2 is a side elevation of the apparatus of the present invention.

Referring to the several views of the drawings there is generally illustrated as 10 the present invention directed to a hurricane simulation testing apparatus for testing the strength and integrity of various structures such as, but not limited to, windows, garage doors, hurricane shutters, storm panels and entry doors.

In accordance with the present invention there is provided a wall structure 12 which is vertically supported in relation to a ground surface 100. The wall 12 may be supported by braces 14 extending between a rear surface 16 of the wall 12 and a fixed wall 110 such as in a building or a warehouse. The wall 12 further includes a front face 18 and at least one air passage hole 19 formed therethrough between the front and rear faces 16, 18.

Figure 3:
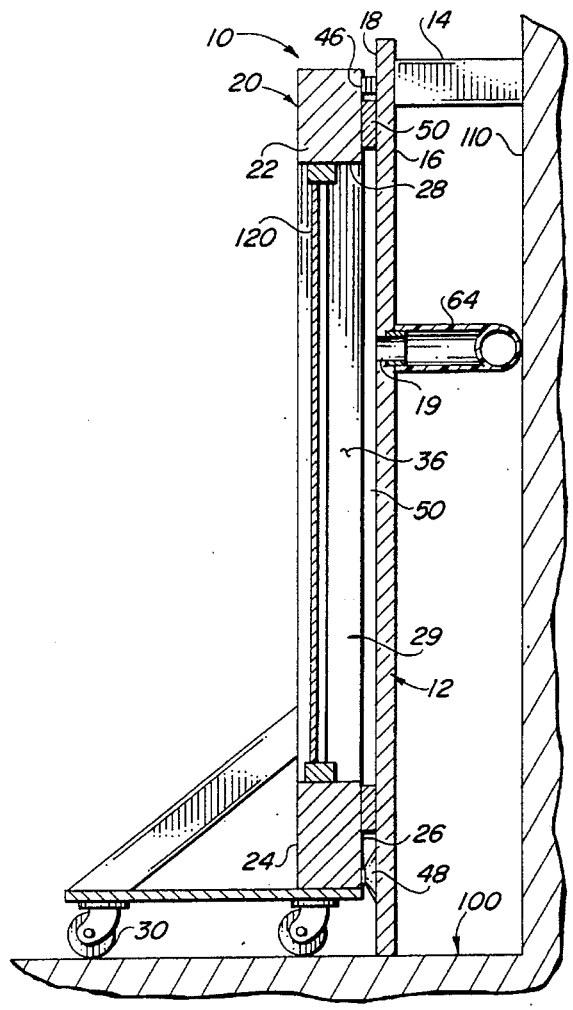
FIG. 3 is a side elevation, in section, of the apparatus of the present invention.

The apparatus 10 further includes a test specimen mounting and support assembly 20 for supporting a test specimen 120 such as a shutter structure to be tested. The test specimen mounting and support assembly 20 includes a frame 22 which is specifically structured and disposed for supporting at least one of the specimen structures 120 to be tested. The frame 22 includes an outer face 24, an opposite inner face 26 and an interior mounting zone 28 defined within and surrounded by the frame for mounting the test specimen 120 in supported, air-tight relation between the opposite outer and inner faces so as to substantially fill the interior mounting zone, as best seen in FIGS. 1 and 3. In order to facilitate an air-tight mounting of the specimen 120 within the frame 22, gaps between the specimen 120 and frame 22 can be filled using foam and/or duct tape. The test specimen 120 is mounted within the frame 22 in generally the same manner as the specimen structure 120 would be normally mounted on a building structure such as a house. In this manner, the integrity of the specimen structure 120 and mounting system can be determined by testing the combined structure and mounting under hurricane type conditions.

The test specimen mounting and support assembly further includes a plurality of wheels, rollers or casters 30 to facilitate movement of the test specimen mounting and support assembly 20 along a ground surface so that various tests such as pressure tests and impact tests can be performed on the test specimen 120.

To perform pressure tests, including increments of pressure testing and cycling of pressure testing, the test specimen mounting and support assembly 20, with the test specimen 120 mounted thereon, is moved into position against the wall 12 so that the inner face 26 of the frame 22 is disposed in mating engagement with the front face 18 of the wall 12. Attachment means 40 are provided for removably attaching the frame 22 to the wall 12 so as to form a cavity 36 between the normally exterior side 122 of the test specimen structure 120, the front face 18 and the surrounding inner sides 29 of the frame 22. The attachment means 40 may be comprised of a series of threaded bolt and nut fasteners, including threaded bolts disposed at spaced intervals and extending from the inner face of the frame 22 for receipt through correspondingly aligned apertures 43 in the wall 12. Once fitted through the apertures, a conventional nut is affixed to the threaded end of the bolt to secure the frame 22 against the wall 12. Alternatively, other means of attachment may be used including clamps 44, magnets 46 on the inner face of the frame 22 and front face 18 of the wall 12 or suction cups 48 on either the front face 18 of the wall 12 or the frame 22.

A seal 50 is further provided on the inner face of the frame 22, and extending entirely thereabout, so as to provide an air-tight seal when the frame is attached to the wall.

A high volume, low pressure blower 60 generates a high volume airflow which is directed through an airflow conduit 64 extending between the blower 60 and the air passage hole in the wall 12, connecting to the air passage hole on the rear face of the wall.

Figure 4:
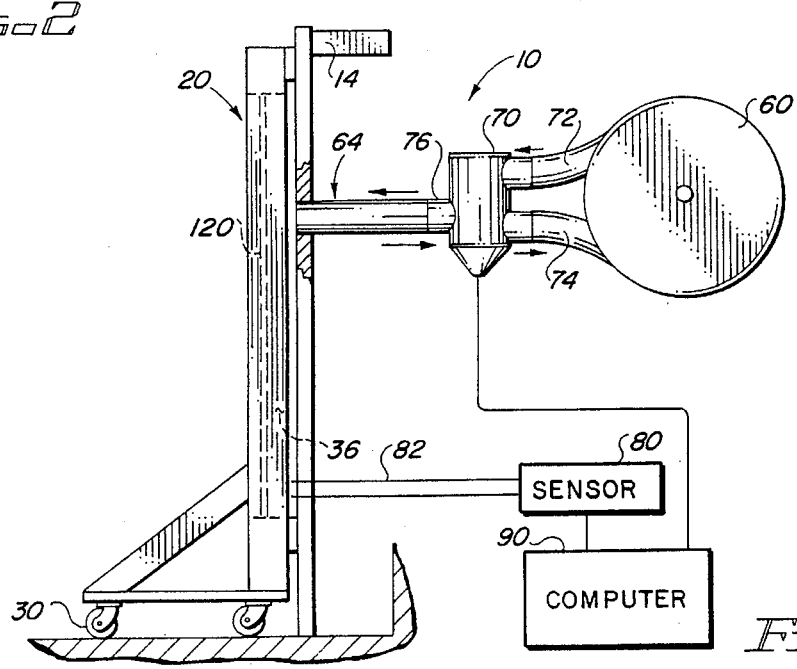
FIG. 4 is a schematic illustration of the present invention.

A diverter valve 70 is fitted inline along the airflow conduit 64 between the blower 60 and the air passage hole. The diverter valve 70 is specifically structured and disposed to selectively direct airflow to the air passage hole so as to progressively increase pressure in the cavity to a predetermined positive pressure level and to further reverse airflow to draw air from the cavity through the air passage hole to progressively decrease pressure in the cavity to a predetermined negative pressure level. As seen in FIGS. 1 and 4, the diverter valve 70 interconnects with the blower 60 via a return 72 and supply line 74. The diverter valve 70 thereafter interconnects with the air passage hole via a main airflow line. The diverter valve is specifically structured to open the return line while closing the supply line and alternatively open the supply line while closing the return line. In this manner, the direction of airflow can be reversed through the main airflow line 76 leading to the air passage hole for either supplying air or withdrawing air from the cavity.

Referring to FIG. 4, the major components of the system of the present invention are illustrated. Specifically, a sensor 80 interconnects to the pressure cavity 36 via a pressure line 82 to measure pressure levels in the cavity. A computer 90 receives the pressure data from the sensor and controls the operation of the diverter valve so as to selectively control the direction of airflow to or from the cavity 36, thereby enabling rapid pressure changes in cavity between positive and negative pressure levels. In this manner, tests such as cycling of pressure can be efficiently performed, completing a cycle of pressure from 0 to maximum pressure and back to the 0 pressure in less than 3 seconds.

Once having complete pressure tests, the test specimen mounting and support assembly 20 can be quickly and efficiently removed from the wall 12 and moved into position for subjecting the outer facing surface 122 of the test specimen 120 (which was previously directed toward the interior pressure cavity) to impact of a projectile, such as a 2"×4", as required during impact testing pursuant to building codes.

While the invention has been shown and described in what is considered to be a practical and preferred embodiment, it is recognized that departures may be made within the spirit and scope of the following claims which, therefore, should not be limited except within the Doctrine of Equivalents.

Now that the invention has been described,
What is claimed is:

1. An apparatus for testing the strength of specimen structures under conditions commonly experienced during a hurricane, said apparatus comprising:

a vertically supported wall having a front face and a rear face, a test specimen mounting and support assembly including a frame structured and disposed for mounting at least one of the specimen structures to be tested, said frame including an outer face, an opposite inner face and an interior mounting zone defined within and surrounded by said frame for mounting the test specimen structure in supported, air-tight relation between said opposite outer and inner faces throughout said interior mounting zone, roller means on said test specimen mounting and support assembly to facilitate movement thereof along a ground surface, attachment means for removably attaching said inner face of said frame to said front face of said wall forming a cavity defined between the test specimen structure, said front face and said surrounding frame, seal means for providing an air-tight sealed attachment between said front face of said wall and said inner face of said frame, said wall including at least one air passage hole formed therethrough between said front and rear faces and in fluid airflow communication with said cavity when said frame is attached to said wall, a high volume, low pressure blower for generating a high volume airflow, an airflow conduit interconnecting between said blower and said air passage hole at said rear face of said wall to facilitate airflow therebetween, a diverter valve interconnected to said airflow conduit inline between said blower and said air passage, said diverter valve being structured and disposed to selectively direct airflow to said air passage hole to progressively increase pressure in said cavity to a predetermined positive pressure level and to further reverse airflow to draw air from said cavity through said air passage hole to progressively decrease pressure in said cavity to a predetermined negative pressure level, pressure sensor means for measuring the pressure level in said cavity, and computer control means interconnected to said pressure sensor means and said diverter valve for monitoring the pressure level in said cavity and operating said diverter valve to control airflow between said diverter valve and said cavity and thereby selectively controlling changes in pressure within said cavity in accordance with predetermined pressure levels.

2. An apparatus for testing the strength and integrity of specimen structures under conditions commonly experienced during a hurricane, said apparatus comprising:

a vertically supported wall having a front face and a rear face, a test specimen mounting and support assembly including a frame structured and disposed for supporting at least one of the specimen structures to be tested, said frame including an outer face, an opposite inner face and an interior mounting zone defined within and surrounded by said frame for mounting the test specimen structure in supported air-tight relation between said opposite outer and inner faces throughout said interior mounting zone, attachment means for removably attaching said inner face of said frame to said front face of said wall forming a cavity defined between the test specimen structure, said front face and said surrounding frame, seal means for providing an air-tight seal attachment between said front face of said wall and said inner face of said frame, said wall including at least one air passage hole formed therethrough between said front and rear faces and in fluid airflow communication with said cavity when said frame is attached to said wall, blower means for generating a high volume airflow, and an airflow conduit interconnecting between said blower means and said air passage hole at said rear face of said wall.

3. An apparatus as set forth in claim 2 wherein said test specimen mounting and support assembly includes roller means to facilitate movement thereof along a ground surface.

4. An apparatus as set forth in claim 3 wherein said blower means includes a high volume, low pressure blower.

5. An apparatus as set forth in claim 4 further including a diverter valve interconnected to said airflow conduit inline between said blower means and said air passage hole, said diverter valve being structured and disposed to selectively direct airflow to said air passage hole to progressively increase pressure in said cavity to a predetermined positive pressure level and to further reverse airflow to draw air from said cavity through said air passage hole to progressively decrease pressure in said cavity to a predetermined negative pressure level.

6. An apparatus as set forth in claim 2 wherein said attachment means includes a plurality of threaded bolt and nut fasteners extending through said wall and said inner face of said frame at spaced intervals about said frame.

7. An apparatus as set forth in claim 2 wherein said attachment means includes a plurality of clamp means removably attachable to said frame and said wall at spaced intervals about said frame.

8. An apparatus as set forth in claim 2 wherein said attachment means includes magnetic bonding means matingly positioned and disposed on said inner face of said frame and said front face of said wall to facilitate magnetic connection of said inner face of said frame to said front face of said wall.

9. An apparatus as set forth in claim 2 wherein said attachment means includes suction means to facilitate attachment of said frame to said front face of said wall.

10. An apparatus as set forth in claim 2 further including pressure sensor means interconnected to said cavity for measuring the pressure level therein.

11. An apparatus as set forth in claim 10 further including computer control means interconnected to said pressure sensor means and said diverter valve for monitoring the pressure level in said cavity and operating said diverter valve to control airflow between said diverter valve and said cavity and thereby selectively controlling changes in pressure within said cavity in accordance with predetermined pressure levels.

* * * * *